US006322552B1

(12) United States Patent
Blenke et al.

(10) Patent No.: US 6,322,552 B1
(45) Date of Patent: **\*Nov. 27, 2001**

(54) ABSORBENT ARTICLES HAVING BELT LOOPS AND AN ADJUSTABLE BELT

(75) Inventors: Timothy James Blenke, Neenah; Laura Linda Elsberg; Jennifer Elizabeth Pozniak, both of Appleton; Jody Dorothy Suprise, Pine River, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/100,681

(22) Filed: Jun. 19, 1998

(51) Int. Cl.[7] ............................. A61F 13/15; A61F 13/20

(52) U.S. Cl. ..................... 604/540; 604/391; 604/392; 604/394

(58) Field of Search ................................. 604/387, 393, 604/385.1, 385.2, 385.01, 385.03, 385.15, 385.29, 385.3, 386, 391, 392–402; 156/164; 2/75–76, 86, 219–221, 236–237, 919

(56) References Cited

U.S. PATENT DOCUMENTS

| | | |
|---|---|---|
| H1558 | 7/1996 | Goulait et al. . |
| H1674 | 8/1997 | Ames et al. . |
| D. 290,780 | 7/1987 | Wistrand . |
| D. 389,320 | 1/1998 | Vinnage et al. . |
| 1,079,479 | 11/1913 | Earnshaw . |
| 1,485,001 | 2/1924 | Wills . |
| 1,657,909 | 1/1928 | Abramovich . |
| 1,705,194 | 3/1929 | Marinsky . |

(List continued on next page.)

FOREIGN PATENT DOCUMENTS

| | | |
|---|---|---|
| 667899 | 4/1996 | (AU) . |
| 2096672 | 11/1993 | (CA) . |
| 2103992 | 2/1994 | (CA) . |
| 2187021 | 10/1995 | (CA) . |
| 2187366 | 10/1995 | (CA) . |
| 0 206 208 | 12/1986 | (EP) . |
| 0 217 032 | 4/1987 | (EP) . |
| 0 251 251 | 1/1988 | (EP) . |

(List continued on next page.)

OTHER PUBLICATIONS

Derwent World Patent Database abstract of FR 2762507 A1: Description of RAHALA, "Baby's Disposable Nappy".
Derwent World Patent Database abstract of JP 6–063076 A: Description of Kao Corp. (Kaos), "Throw Away Diaper Or Nappy".

(List continued on next page.)

*Primary Examiner*—John G. Weiss
*Assistant Examiner*—K. M. Reichle
(74) *Attorney, Agent, or Firm*—Jeffrey B. Curtin

(57) ABSTRACT

Disposable absorbent articles which include an outer cover, an absorbent chassis, an adjustable belt and belt loops are described. The adjustable belt is located in one waist region of the absorbent article and includes a fastener on each of it's opposed end portions. The belt loops are located inward from and adjacent to each of the fasteners on the adjustable belt and the longitudinal ends of the belt loops are attached to the absorbent article to slidably contain the adjustable belt between the belt loops and the waist region. The fasteners on the adjustable belt are configured to releasably engage the opposite waist region of the absorbent article. Desirably, the adjustable belt and belt loops are located on an inner surface of the absorbent article such as the bodyfacing surface of the outer cover or the bodyside liner. The absorbent article may also include fasteners on the belt loops to provide another pair of fasteners.

32 Claims, 4 Drawing Sheets

U.S. PATENT DOCUMENTS

| | | |
|---|---|---|
| 1,762,468 | 6/1930 | Brewer . |
| 1,963,334 | 6/1934 | Neilson . |
| 2,201,255 | 5/1940 | Wilson, Jr. . |
| 2,242,977 | 5/1941 | Marcos . |
| 2,475,175 | 7/1949 | Cadous . |
| 2,477,914 | 8/1949 | Webb . |
| 2,545,761 | 3/1951 | Brink . |
| 2,570,963 | 10/1951 | Mesmer . |
| 2,630,120 | 3/1953 | Nielson . |
| 2,630,806 * | 3/1953 | Kiscaden ............................ 604/392 |
| 2,743,725 | 5/1956 | Matthews . |
| 2,801,632 | 8/1957 | Bruner et al. . |
| 2,808,831 | 10/1957 | Winslett . |
| 2,830,589 | 4/1958 | Doner . |
| 2,833,282 | 5/1958 | Moore . |
| 2,910,982 | 11/1959 | Woodward . |
| 2,931,361 | 4/1960 | Sostrin . |
| 3,039,466 | 6/1962 | Wilson . |
| 3,077,193 | 2/1963 | Mann . |
| 3,610,244 | 10/1971 | Jones, Sr. . |
| 3,638,651 | 2/1972 | Torr . |
| 3,653,381 | 4/1972 | Warnken . |
| 3,825,006 | 7/1974 | Ralph . |
| 3,882,871 | 5/1975 | Taniguchi . |
| 4,024,867 | 5/1977 | Mesek . |
| 4,051,853 | 10/1977 | Egan, Jr. . |
| 4,051,854 | 10/1977 | Aaron . |
| 4,066,081 | 1/1978 | Schaar . |
| 4,074,716 | 2/1978 | Schaar . |
| 4,089,068 | 5/1978 | Swallow . |
| 4,090,516 | 5/1978 | Schaar . |
| 4,205,679 | 6/1980 | Repke et al. . |
| 4,210,143 | 7/1980 | De Jonckheere . |
| 4,337,771 | 7/1982 | Pieniak et al. . |
| 4,409,049 * | 10/1983 | Passafiume et al. ................ 156/164 |
| 4,410,327 | 10/1983 | Baggaley . |
| 4,500,316 | 2/1985 | Damico . |
| 4,515,595 | 5/1985 | Kievit et al. . |
| 4,522,853 | 6/1985 | Szonn et al. . |
| 4,525,407 | 6/1985 | Ness . |
| 4,563,185 | 1/1986 | Reiter . |
| 4,568,341 | 2/1986 | Mitchell et al. . |
| 4,581,772 | 4/1986 | Smith . |
| 4,596,055 | 6/1986 | Aach et al. . |
| 4,598,528 | 7/1986 | McFarland et al. . |
| 4,604,096 | 8/1986 | Dean et al. . |
| 4,610,680 | 9/1986 | LaFleur . |
| 4,610,681 | 9/1986 | Strohbeen et al. . |
| 4,615,695 | 10/1986 | Cooper . |
| 4,617,022 | 10/1986 | Pigneul et al. . |
| 4,619,649 | 10/1986 | Roberts . |
| 4,623,339 | 11/1986 | Ciraldo et al. . |
| 4,630,320 | 12/1986 | Van Gompel . |
| 4,663,220 | 5/1987 | Wisneski et al. . |
| 4,675,918 | 6/1987 | O'Brien . |
| 4,699,622 | 10/1987 | Toussant et al. . |
| 4,704,116 | 11/1987 | Enloe . |
| 4,726,874 | 2/1988 | Van Vliet . |
| 4,728,326 | 3/1988 | Gilles . |
| 4,743,239 | 5/1988 | Cole . |
| 4,747,846 | 5/1988 | Boland et al. . |
| 4,753,646 | 6/1988 | Enloe . |
| 4,753,650 | 6/1988 | Williams . |
| 4,798,603 | 1/1989 | Meyer et al. . |
| 4,801,485 | 1/1989 | Sallee et al. . |
| 4,808,252 | 2/1989 | Lash . |
| 4,826,499 | 5/1989 | Ahr . |
| 4,850,988 | 7/1989 | Aledo et al. . |
| 4,850,992 | 7/1989 | Amaral et al. . |
| 4,857,067 | 8/1989 | Wood et al. . |
| 4,883,481 | 11/1989 | Blanchard . |
| 4,892,598 | 1/1990 | Stevens et al. ................ 156/91 |
| 4,904,252 | 2/1990 | Fitzgerald . |
| 4,909,802 | 3/1990 | Ahr et al. . |
| 4,911,702 | 3/1990 | O'Leary et al. . |
| 4,917,682 | 4/1990 | Lancaster et al. . |
| 4,936,840 | 6/1990 | Proxmire . |
| 4,937,887 | 7/1990 | Schreiner . |
| 4,938,753 | 7/1990 | Van Gompel et al. . |
| 4,944,733 | 7/1990 | Casale . |
| 4,961,736 | 10/1990 | McCloud . |
| 4,988,346 | 1/1991 | Pfekkerkorn . |
| 4,998,929 | 3/1991 | Bjorksund et al. . |
| 5,019,072 | 5/1991 | Polski . |
| 5,019,073 | 5/1991 | Roessler et al. . |
| 5,040,244 | 8/1991 | Tubbs . |
| 5,062,839 | 11/1991 | Anderson . |
| 5,066,289 | 11/1991 | Polski . |
| 5,069,678 | 12/1991 | Yamamoto et al. . |
| 5,074,854 | 12/1991 | Davis . |
| 5,087,253 | 2/1992 | Cooper . |
| 5,106,382 | 4/1992 | Henry . |
| 5,106,385 | 4/1992 | Allen et al. . |
| 5,110,403 | 5/1992 | Ehlert . |
| 5,112,326 | 5/1992 | Quadrini . |
| 5,135,522 | 8/1992 | Fahrenkrug et al. . |
| 5,140,757 | 8/1992 | Terada . |
| 5,163,932 | 11/1992 | Nomura et al. . |
| 5,170,505 | 12/1992 | Rohrer . |
| 5,176,668 | 1/1993 | Bernardin . |
| 5,176,670 | 1/1993 | Roessler et al. . |
| 5,176,672 | 1/1993 | Bruemmer et al. . |
| 5,185,011 | 2/1993 | Strasser . |
| 5,186,779 | 2/1993 | Tubbs . |
| 5,192,606 | 3/1993 | Proxmire et al. . |
| 5,226,992 | 7/1993 | Morman . |
| 5,242,436 | 9/1993 | Weil et al. . |
| 5,275,590 | 1/1994 | Huffman et al. . |
| 5,304,162 | 4/1994 | Kuen . |
| 5,340,431 | 8/1994 | Terada . |
| 5,358,500 | 10/1994 | Lavon et al. . |
| 5,368,584 | 11/1994 | Clear et al. . |
| 5,368,585 | 11/1994 | Dokken . |
| 5,370,632 | 12/1994 | Beplate . |
| 5,370,634 | 12/1994 | Ando et al. . |
| 5,373,587 | 12/1994 | Sexton . |
| 5,374,262 | 12/1994 | Keuhn, Jr. et al. . |
| 5,383,872 | 1/1995 | Roessler et al. . |
| 5,386,595 | 2/1995 | Kuen et al. . |
| 5,397,639 | 3/1995 | Tollini . |
| 5,399,219 | 3/1995 | Roessler et al. . |
| 5,401,275 | 3/1995 | Flug et al. ............................ 604/391 |
| 5,423,789 | 6/1995 | Kuen . |
| 5,445,628 | 8/1995 | Gipson et al. . |
| 5,451,219 | 9/1995 | Suzuki et al. . |
| 5,462,541 | 10/1995 | Bruemmer et al. . |
| 5,489,282 | 2/1996 | Zehner et al. . |
| 5,499,978 | 3/1996 | Buell et al. . |
| 5,500,063 | 3/1996 | Jessup . |
| 5,509,915 | 4/1996 | Hanson et al. . |
| 5,527,302 | 6/1996 | Endres et al. . |
| 5,531,731 | 7/1996 | Brusky . |
| 5,531,732 | 7/1996 | Wood . |
| 5,537,722 | 7/1996 | Niederhofer et al. . |
| 5,540,796 | 7/1996 | Fries . |
| 5,545,158 | 8/1996 | Jessup . |
| 5,545,275 | 8/1996 | Herrin et al. . |
| 5,554,146 | 9/1996 | Niederhofer et al. . |
| 5,562,650 | 10/1996 | Everett et al. . |
| 5,569,232 | 10/1996 | Roe et al. . |
| 5,569,234 | 10/1996 | Buell et al. . |

| | | | | | | |
|---|---|---|---|---|---|---|
| 5,571,586 | 11/1996 | Gobran . | | 2 288 314 | 10/1995 | (GB) . |
| 5,575,784 | 11/1996 | Ames-Ooten et al. . | | 2 288 315 | 10/1995 | (GB) . |
| 5,582,606 | 12/1996 | Bruemmer et al. . | | 2 288 316 | 10/1995 | (GB) . |
| 5,591,152 | 1/1997 | Buell et al. . | | 2 291 783 | 2/1996 | (GB) . |
| 5,593,401 | 1/1997 | Sosalla et al. . | | 2 294 867 | 5/1996 | (GB) . |
| 5,601,546 | 2/1997 | Tanji et al. . | | 2 297 473 | 6/1996 | (GB) . |
| 5,607,416 | 3/1997 | Yamamoto et al. . | | 2 308 290 | 6/1997 | (GB) . |
| 5,611,789 | 3/1997 | Seth . | | 6-77718 | 11/1994 | (JP) . |
| 5,618,366 | 4/1997 | Suekane . | | 7-213553 | 8/1995 | (JP) . |
| 5,624,420 | 4/1997 | Bridges et al. . | | 7-227407 | 8/1995 | (JP) . |
| 5,624,424 | 4/1997 | Saisaka et al. . | | 7-255773 | 10/1995 | (JP) . |
| 5,624,428 | 4/1997 | Sauer . | | 7-299094 | 11/1995 | (JP) . |
| 5,624,429 | 4/1997 | Long et al. . | | 8-229072 | 9/1996 | (JP) . |
| 5,626,574 | 5/1997 | Sasaki et al. . | | 9-287 | 5/1997 | (JP) . |
| 5,628,738 | 5/1997 | Suekane . | | 9-287 U | 5/1997 | (JP) . |
| 5,629,063 | 5/1997 | Gobran . | | 11-47188 | 2/1999 | (JP) . |
| 5,634,916 | 6/1997 | Lavon et al. . | | 83/04163 | 12/1983 | (WO) . |
| 5,656,111 | 8/1997 | Dilnik et al. . | | 90/07313 | 7/1990 | (WO) . |
| 5,662,637 | 9/1997 | Kitaoka et al. . | | 91/04724 | 4/1991 | (WO) . |
| 5,662,638 | 9/1997 | Johnson et al. . | | 91/08725 | 6/1991 | (WO) . |
| 5,665,084 | 9/1997 | Richmond . | | 92/22274 | 12/1992 | (WO) . |
| 5,669,897 | 9/1997 | Lavon et al. . | | 93/09742 | 5/1993 | (WO) . |
| 5,685,874 | 11/1997 | Buell et al. . | | 94/17768 | 8/1994 | (WO) . |
| 5,690,626 | 11/1997 | Suzuki et al. . | | 95/01148 | 1/1995 | (WO) . |
| 5,690,627 | 11/1997 | Clear et al. . | | 95/02383 | 1/1995 | (WO) . |
| 5,693,038 | 12/1997 | Suzuki et al. . | | 95/13772 | 5/1995 | (WO) . |
| 5,707,364 | 1/1998 | Coates . | | 95/22951 | 8/1995 | (WO) . |
| 5,711,832 | 1/1998 | Glaug et al. . | | 95/27460 | 10/1995 | (WO) . |
| 5,725,518 * | 3/1998 | Coates ................................... 604/391 | | 95/27462 | 10/1995 | (WO) . |
| 5,759,317 | 6/1998 | Justmann . | | 95/29657 | 11/1995 | (WO) . |
| 5,772,825 | 6/1998 | Schmitz . | | 96/03101 | 2/1996 | (WO) . |
| 5,788,685 | 8/1998 | Ronnberg et al. . | | 96/18315 | 6/1996 | (WO) . |
| 5,788,797 | 8/1998 | Herrin et al. . | | 96/32084 | 10/1996 | (WO) . |
| 5,795,433 | 8/1998 | Niedermeyer . | | 97/15260 | 5/1997 | (WO) . |
| 5,827,259 | 10/1998 | Laux et al. . | | 97/23186 | 7/1997 | (WO) . |
| 5,827,260 | 10/1998 | Suzuki et al. . | | 97/25951 | 7/1997 | (WO) . |
| 5,830,206 | 11/1998 | Larsson ................................ 604/390 | | 97/31605 | 9/1997 | (WO) . |
| 5,855,574 | 1/1999 | Kling et al. ......................... 604/392 | | 97/32555 | 9/1997 | (WO) . |
| 5,876,531 | 3/1999 | Jacobs et al. . | | 97/33547 | 9/1997 | (WO) . |
| 5,897,545 | 4/1999 | Kline et al. .......................... 604/386 | | 97/46197 | 12/1997 | (WO) . |
| 5,904,802 | 5/1999 | Niedermeyer . | | 97/47265 | 12/1997 | (WO) . |
| 5,919,334 | 7/1999 | Niedermeyer . | | 98/03140 | 1/1998 | (WO) . |
| 6,022,430 | 2/2000 | Blenke et al. . | | 98/18421 | 5/1998 | (WO) . |
| 6,022,431 | 2/2000 | Blenke et al. . | | 98/56328 | 12/1998 | (WO) . |
| 6,022,432 | 2/2000 | Elsberg et al. . | | 99/07319 | 2/1999 | (WO) . |
| 6,036,805 | 3/2000 | McNichols . | | | | |
| B1 4,315,508 | 11/1988 | Bolick . | | | | |
| B1 4,964,860 | 1/1994 | Gipson et al. . | | | | |

FOREIGN PATENT DOCUMENTS

| | | |
|---|---|---|
| 0 463 276 | 1/1992 | (EP) . |
| 0 532 034 | 3/1993 | (EP) . |
| 0 544 703 | 6/1993 | (EP) . |
| 0 696 911 | 2/1996 | (EP) . |
| 0 753 292 | 1/1997 | (EP) . |
| 0 487 758 | 3/1997 | (EP) . |
| 0597331 | 11/1997 | (EP) . |
| 0 809 992 | 12/1997 | (EP) . |
| 0 878 180 | 11/1998 | (EP) . |
| 1 520 740 | 8/1978 | (GB) . |
| 2 244 422 | 12/1991 | (GB) . |
| 2 267 024 | 11/1993 | (GB) . |

OTHER PUBLICATIONS

Derwent World Patent Database abstract of JP 95–044941 B2: Description of Zuiko KK (Zuik–N), "Simple Solid Diaper For Eliminating Waste of Material by Using Square Shape".

Derwent World Patent Database abstract of JP 9–276334 A: Description of Kao Corp (Kaos), "Disposable Baby Nappy".

Derwent World Patent Database abstract of JP 11–070143 A: Description of TOYO EISAI KK (TOEI–N), "Disposable Diaper For Adults And Children".

Derwent World Patent Database abstract of JP 11–076299 A: Description of UNI–CHARM KK (UNIC–N), "Disposable Diaper".

* cited by examiner

ABSORBENT ARTICLES HAVING BELT LOOPS AND AN ADJUSTABLE BELT

FIELD OF THE INVENTION

The present invention relates to disposable absorbent articles which are adapted to contain body exudates. More particularly, the present invention relates to absorbent articles having belt loops and an adjustable belt.

BACKGROUND OF THE INVENTION

It is desired that absorbent articles such as diapers, training pants or incontinence garments provide a dose, comfortable fit about the wearer and contain body exudates. Moreover, it is desirable that such absorbent articles, after being soiled, can be removed from the wearer in a convenient and clean manner without undesirably soiling the care giver or surrounding area such as the clothes of the wearer. In certain circumstances, it is also desirable that such absorbent anices are capable Qf being pulled up or down over the hips of the wearer to allow the wearer or caregiver to easily pull the article on and easily remove the article if it has not been soiled. For example, such absorbent articles can assist in the toilet training of children.

Conventional diapers have typically included a front waist portion and a back waist portion which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost comers of the diaper in the back waist region of the diaper and a complimentary fastener, such as a taping panel, located on the outer surface of the outer cover of the diaper in the front waist portion of the diaper. In such a configuration, the diaper has been positioned between the legs of the wearer and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the care giver.

However, such conventional diapers are not provided in a prefastened configuration and thus are not configured to be pulled up or down over the hips of the wearer when the fasteners are attached. Moreover, such conventional diapers generally have one set of fasteners which must be disengaged and reattached to further conform the waist portions of the diaper to the wearer. Such disengagement and reattachment can be difficult to accomplish when the wearer is active.

Several attempts have been made to provide absorbent articles which fit the waist of the wearer to effectively contain body exudates, are capable of being pulled up or down over the hips of the wearer and provide ease of cleaning and removal after being soiled. For example, some conventional absorbent articles, such as conventional training pants, have included integral side panels which connect the front waist portion to the back waist portion of the absorbent article. The side panels have been made stretchable such that the waist opening of the absorbent article can expand to allow the absorbent article to be pulled up or down over the hips of the wearer if desired. Such side panels have also been designed such that they may be tom to remove the training pant from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely which can undesirably result in leaks. As a result, many of such artides have not contained bodily exudates as effectively as conventional diaper-type articles which can be adjusted to achieve a more conforming fit to the wearer. Moreover, the removal of soiled absorbent articles which have integral side panels, such as conventional training pants, has not been completely satisfactory. For example, the side panels have been difficult to tear when attempting to remove the article from the waist of the wearer instead of pulling the article down over the hips of the wearer.

Accordingly, despite the attempts to develop improved absorbent articles, there remains a need for absorbent articles which can provide the benefits of both conventional training pants and conventional diapers. That is, there remains a need for absorbent articles which conform to the wearer to effectively contain bodily exudates, which are capable of being pulled up and down over the hips and buttocks of the wearer without opening, and which are readily secured about and removed from the wearer in a convenient and clean manner.

SUMMARY OF THE INVENTION

In response to the difficulties and problems discussed above, new disposable absorbent articles having belt loops and an adjustable belt have been discovered. In one aspect, the present invention concerns a disposable absorbent article which defines an absorbent, a front waist region, a back waist region, and a crotch region which extends between and connects the waist regions. The absorbent article includes an adjustable belt located in one of the waist regions of the absorbent article. The adjustable belt defines a pair of opposed end portions and a fastener on each of the opposed end portions. The absorbent also includes a belt loop located inward from and adjacent to each of the fasteners on the adjustable belt. Each of the belt loops define a pair of opposed longitudinal ends which are attached to the waist region of the absorbent article to slidably contain the adjustable belt between the belt loops. The fasteners on the adjustable belt are configured to releasably engage the opposite waist region of the absorbent article.

In another aspect, the present invention concerns a disposable absorbent article which defines an absorbent, a front waist region, a back waist region, a crotch region which extends between and connects the waist regions, a pair of opposed side edges and a pair of opposed waist edges. The absorbent article includes an outer cover and an adjustable belt which is attached to the outer cover using belt loops. The adjustable belt defines a pair of opposed end portions each of which has a secondary fasteners attached thereto. A belt loop is located inward from and adjacent to each of the secondary fasteners on the adjustable belt. Each of the belt loops defines a pair of longitudinally opposed ends which are attached to a bodyfacing surface of the outer cover in one waist region of the absorbent article to slidably contain the adjustable belt between the belt loops and the bodyfacing surface of the outer cover. The secondary fasteners on the adjustable belt are configured to releasably engage the garment facing surface of the outer cover in the opposite waist region of the absorbent article. In a particular embodiment, each of the belt loops includes a primary fastener on a bodyfacing surface thereof which is also configured to releasably engage the garment facing surface of the outer cover in the opposite waist region to provide a dual fastening system.

In yet another aspect, the present invention concerns a prefastened disposable absorbent article which defines an absorbent, a front waist region, a back waist region, a crotch region which extends between and connects the waist regions, a pair of opposed side edges and a pair of opposed waist edges. The prefastened absorbent article includes an outer cover, an adjustable belt attached to the outer cover with belt loops, a pair of secondary fasteners and a pair of primary fasteners. The adjustable belt defines a pair of opposed end portions each of which includes a secondary fastener attached thereto. A belt loop is located inward from and adjacent to each of the secondary fasteners on the adjustable belt Each of the belt loops defines a pair of longitudinally opposed ends which are attached to the outer cover to slidably contain the adjustable belt between the belt loops and the outer cover. A primary fastener is located on each of the belt loops and is releasably engaged to the outer cover in the opposite waist region of the absorbent article to provide the prefastened absorbent article. The secondary fasteners on the adjustable belt are configured to releasably engage the outer cover in the opposite waist region to further conform said the regions to a wearer's body after the prefastened absorbent article has been placed on the wearer.

The present invention advantageously provides disposable absorbent articles which include belt loops and an adjustable belt for improved fit and performance. In particular, the present invention provides disposable absorbent articles which include an adjustable belt which is slidably contained by belt loops. The absorbent article of the present invention is capable of being reliably pulled up or down over the hips of the wearer to assist in the toilet training of the wearer similar to conventional training pants. After being pulled up over the hips of the wearer, the adjustable belt of the absorbent article can be used to further conform the waist of the article to the wearer's body for improved fit and leakage control. Moreover, similar to conventional diapers, the absorbent article of the present invention can advantageously be applied to and removed from the wearer after it has been soiled with relative ease and cleanliness. Further, the use of multiple fasteners can result in improved reliability in maintaining the article on the wearer.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention concerns disposable absorbent articles which are configured to closely conform to the body of the wearer to effectively contain body exudates and methods of making the same. The absorbent articles may be provided in a prefastened configuration such that they can be pulled up or down over the hips and buttocks of the wearer and are configured to be easily secured to and removed directly from the waist of the wearer. As such, the absorbent articles of the present invention can function in a similar manner to conventional training pants when left in the prefastened configuration or in a similar manner to conventional diapers when in an unfastened configuration. The disposable absorbent articles are adapted to be worn adjacent to the body of a wearer to absorb and contain various exudates discharged from the body. As used herein, the term "disposable" refers to articles which are intended to be discarded after a limited use and which are not intended to be laundered or otherwise restored for reuse.

The disposable absorbent articles of the present invention will be described in terms of a disposable diaper article which is adapted to be worn by infants about the lower torso. In particular, the absorbent articles will be described in terms of a disposable absorbent diaper having an adjustable belt. It is understood that the articles of the present invention are equally adaptable for other types of absorbent articles such as adult incontinent products, training pants, feminine hygiene products, other personal care or health care garments, and the like.

Figure 1:
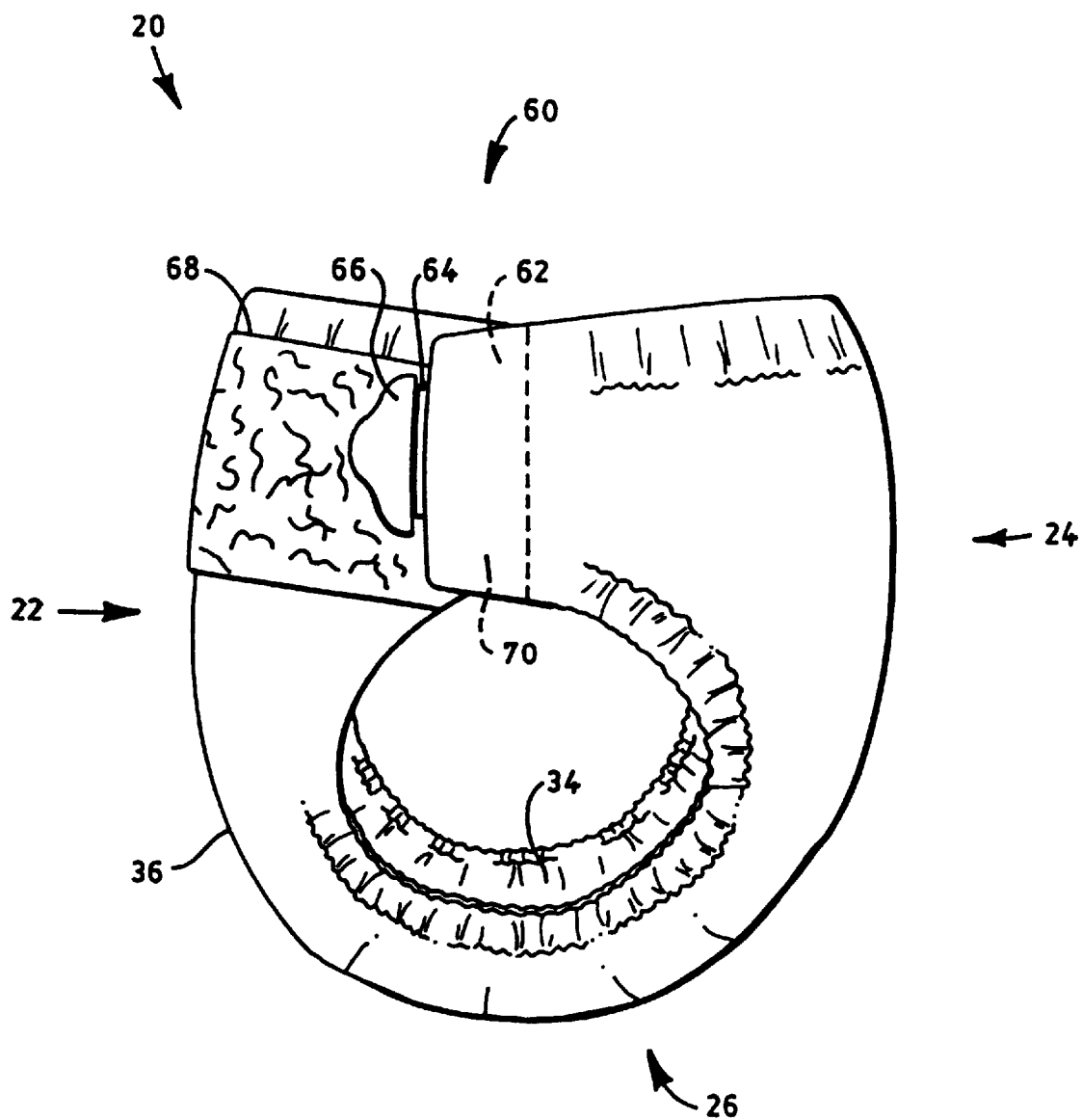
FIG. 1 representatively shows a side view of an example of a disposable absorbent article according to the present invention.
Figure 2:
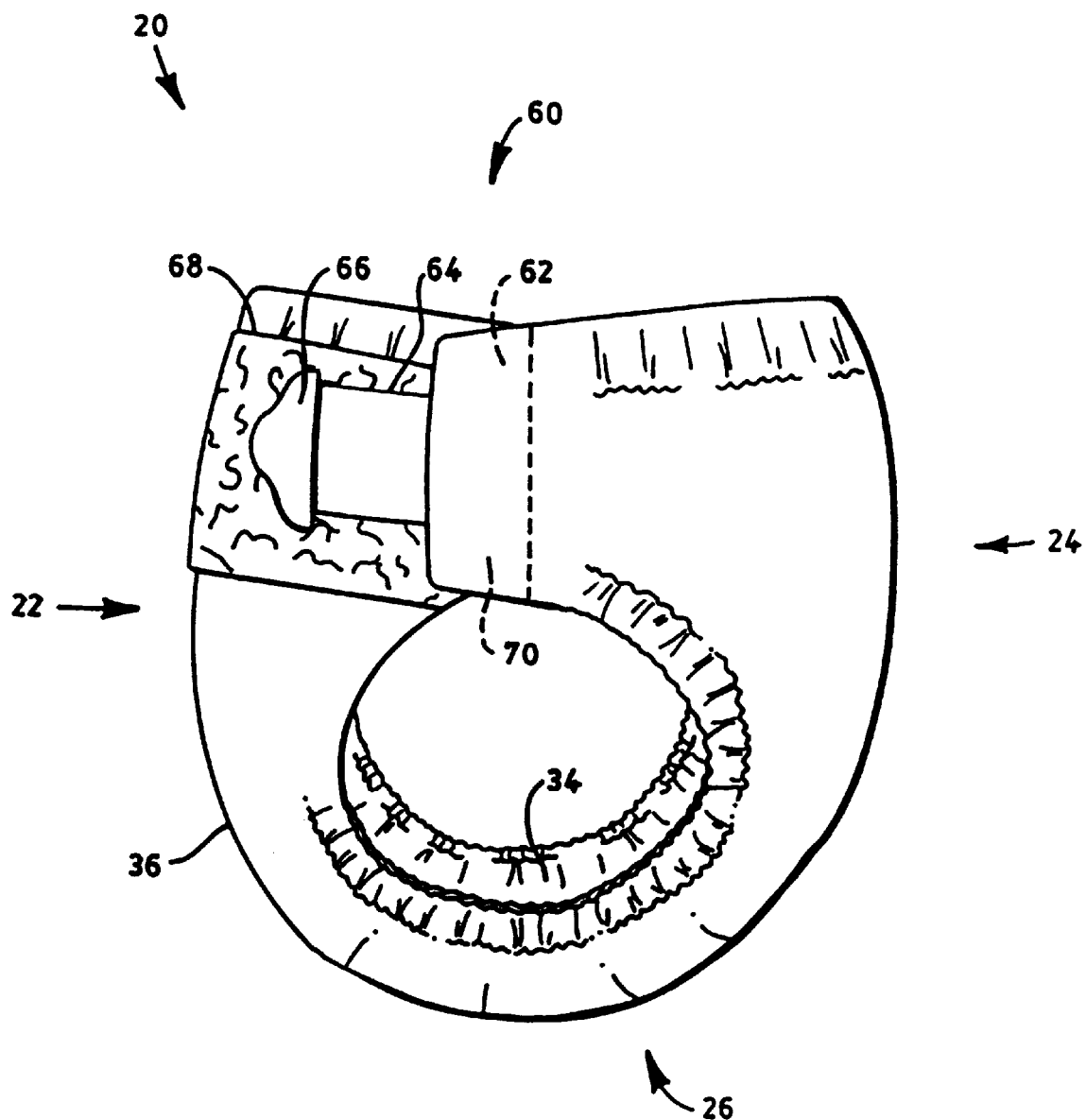
FIG. 2 representatively shows a side view of the disposable absorbent article of FIG. 1 wherein the adjustable belt has been extended to conform the waist regions of the article to the waist of the wearer, FIG. 3 representatively shows a plan view of the disposable absorbent article of FIG. 1 in an unfastened, stretched and laid flat condition with the surface of the article which contacts the wearer facing the viewer and is partly cut-away to reveal components of the disposable absorbent article.
Figure 3:
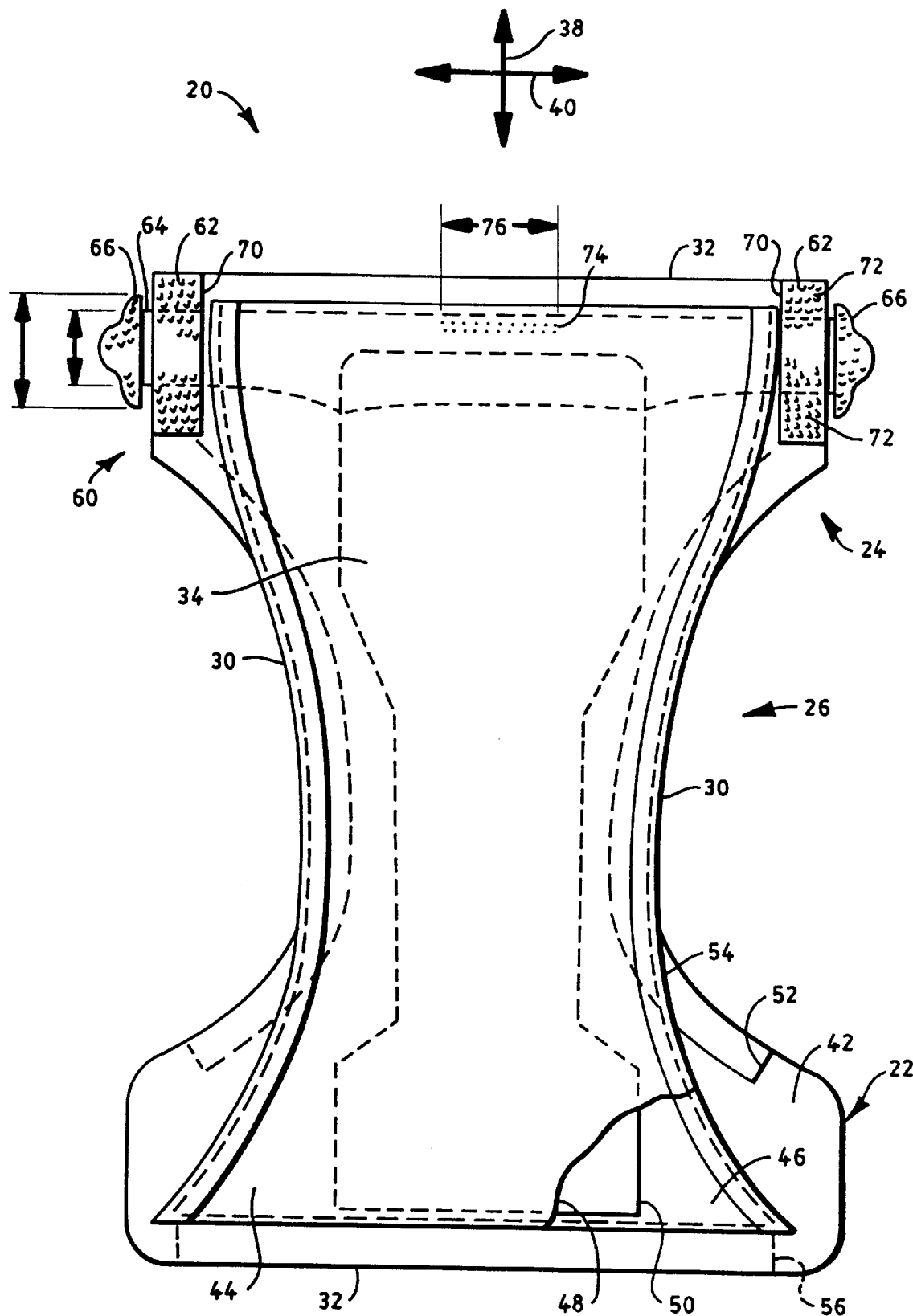
Figure 4:
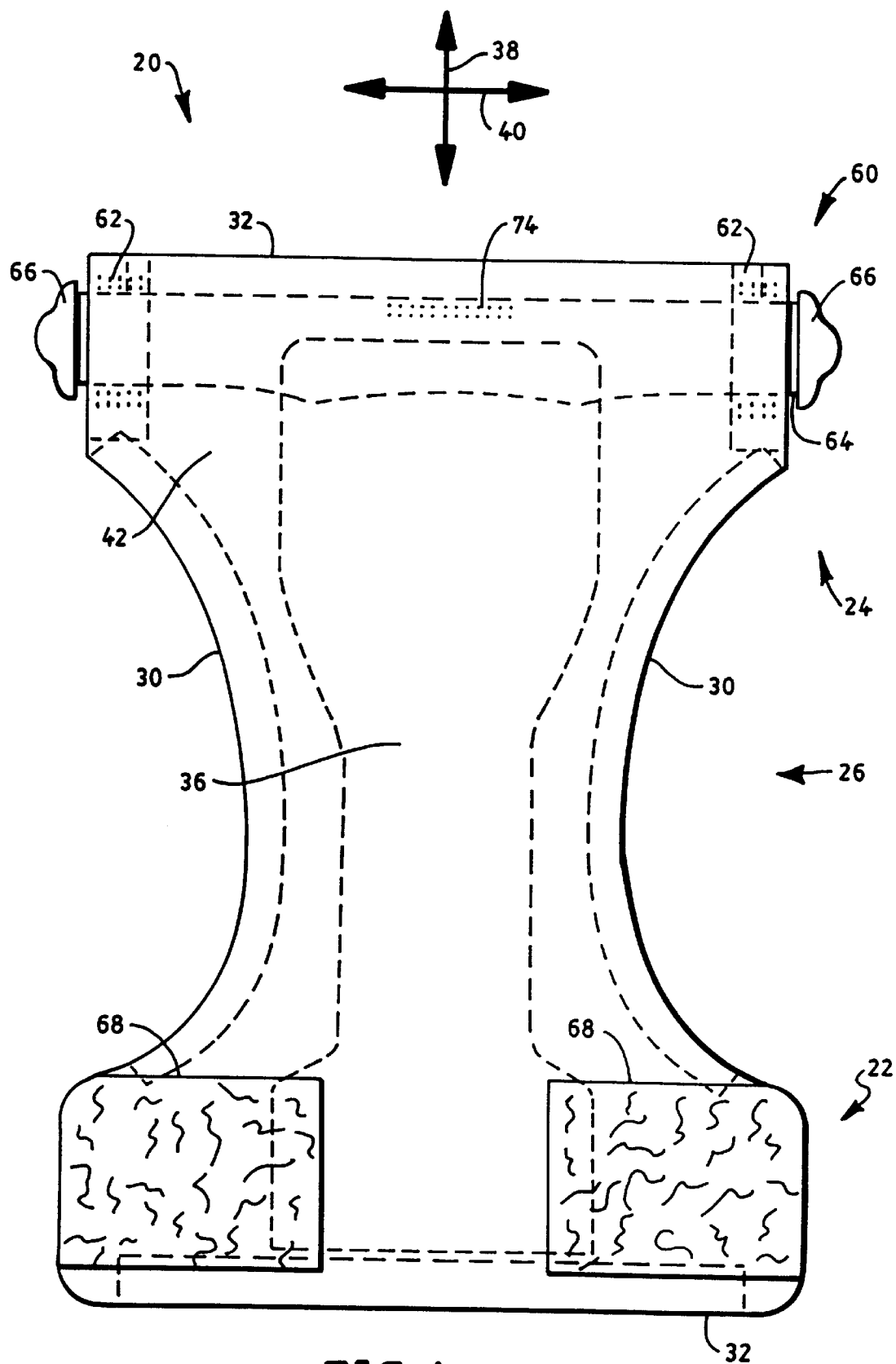
FIG. 4 representatively shows a plan view of the disposable absorbent article of FIG. 1 in an unfastened, stretched and laid flat condition with the surface of the article which contacts the wearer's clothing facing the viewer.

FIGS. 1 and 2 representatively illustrate an example of a disposable diaper, as generally indicated at 20, which includes belt loops and an adjustable belt according to the present invention. FIGS. 3 and 4 representatively illustrate the diaper of FIG. 1 in an unfastened, stretched and laid flat configuration. As illustrated in FIGS. 1–4, the diaper 20 defines a front waist region 22, a back waist region 24, and a crotch region 26 which extends between and connects the front and back waist regions 22 and 24. The diaper 20 further defines a pair of laterally opposed side edges 30, a pair of longitudinally opposed waist edges 32, an interior surface 34 which is configured to contact the wearer, an outer surface 36 opposite the interior surface 34, a longitudinal direction 38 and a lateral direction 40.

The front waist region 22 comprises the portion of the diaper 20 which, when worn, is positioned on the front of the wearer while the back waist region 24 comprises the portion of the diaper 20 which, when worm, is positioned on the back of the wearer. The crotch region 26 of the diaper 20 comprises the portion of the diaper 20 which, when worm, is positioned between the legs of the wearer and covers the lower torso of the wearer. The laterally opposed side edges 30 of the diaper 20 generally define leg openings which may be curvilinear. The waist edges 32 of the diaper 20 are configured to encircle the waist of the wearer when worn and provide a waist opening when fastened which defines a waist perimeter dimension.

The illustrated diaper 20 includes an outer cover 42, an absorbent chassis 44 and a multi-functional fastening system 60. The absorbent chassis 44 includes a backsheet 46, a bodyside liner 48 which is connected to the backsheet 46 in a superposed relation, and an absorbent core 50 which is located between the bodyside liner 48 and the backsheet 46. The fastening system 60 includes a pair of primary fasteners 62, an adjustable belt 64, a pair of secondary fasteners 66 attached to the laterally opposed end portions of the adjustable belt 64 and a pair of belt loops 70. In the illustrated embodiment, the adjustable belt 64 is slidably contained between the belt loops 70 and the outer cover 42 of the diaper 20.

The absorbent chassis 44 is configured to contain and/or absorb any body exudates discharged from the wearer. Whereas, the outer cover 42, primary fasteners 62, adjustable belt 64 and secondary fasteners 66 are configured to maintain the diaper 20 about the waist of the wearer, conceal the absorbent chassis 44 from view, and provide a garment-like appearance. The diaper 20 may further include leg elastics 52, containment flaps 54 and waist elastic 56 as are known to those skilled in the art. It should be recognized that individual components of the diaper 20 may be optional depending upon the intended use of the diaper 20.

A suitable arrangement for the different components of the diaper of the present invention is described in U.S. patent application Ser. No. 08/907,585 entitled "A MULTI-FUNCTIONAL FASTENER FOR DISPOSABLE ABSORBENT ARTICLES" and filed Aug. 8, 1997 in the name of J. Suprise, the disclosure of which is hereby incorporated by reference. Methods of making the diaper of the present invention are described in a U.S. patent application entitled "METHODS OF MAKING ABSORBENT ARTICLES HAVING AN ADJUSTABLE BELT" filed herewith in the name of Blenke et al. and having the disclosure of which is hereby incorporated by reference.

As representatively illustrated in FIGS. 1–4, the outer cover 42 of the diaper 20 may suitably be composed of a material which is either liquid permeable or liquid impermeable. Since the absorbent chassis 44 of the different aspects of the present invention is designed to contain the body exudates discharged from the wearer, it is generally not necessary that the outer cover 42 be liquid impermeable. For example, the outer cover 42 may include various woven or nonwoven materials such as spunbond material, meltblown material, cotton material, rayon material or combinations thereof such as a spunbond-meltblown-spunbond (SMS) laminate material. The outer cover 42 may otherwise be at least partially liquid impermeable to further prevent any leakage of body exudates. For example, a typical outer cover 42 can be manufactured from a thin plastic film or other flexible liquid-impermeable material, woven or nonwoven fibrous layers, microporous "breathable" materials, elastic materials and combinations thereof.

The absorbent chassis 44 of the diaper 20 is suitably connected to the outer cover 42 to provide the disposable diaper 20. The absorbent chassis 44 may be connected to the outer cover 42 in manners well known to those skilled in the art. For example, the absorbent chassis 44 may be bonded to the outer cover 42 using adhesive, thermal or ultrasonic bonding techniques known to those skilled in the art. Alternatively, the absorbent chassis 44 may be connected to the outer cover 42 using conventional fasteners such as buttons, hook and loop type fasteners, adhesive tape fasteners, and the like. The other components of the diaper 20 may be suitably connected together using similar means.

Desirably, the absorbent chassis 44 is connected to the outer cover 42 only at or adjacent the waist edges 32 of the outer cover 42 thereby creating a front attached portion, a back attached portion and an unattached portion which extends between and connects the attached portions. The unattached portion of the absorbent chassis 44 remains substantially unattached to the outer cover 42 and is generally configured to fit between the legs of the wearer and at least partially cover the lower torso of the wearer when in use. As a result, the unattached portion is generally the portion of the absorbent chassis 44 which is configured to initially receive the body exudates from the wearer. Thus, the absorbent chassis 44 is connected to the outer cover 42 in such a manner to secure the chassis 44 in place while not adversely restricting the movement of the outer cover 42 in use. Alternatively, the absorbent chassis 44 may be attached to the outer cover 42 along the entire longitudinal length of the absorbent chassis 44 or any portion thereof or along only the outer periphery of the absorbent chassis 44.

As representatively illustrated in FIG. 3, the absorbent chassis 44 according to the present invention may include a backsheet 46, a bodyside liner 48 which is connected to the backsheet 46 in a superposed relation, and an absorbent core 50 which is located between the bodyside liner 48 and the backsheet 46. In alternative configurations wherein the outer cover 42 is at least partially resistant to the flow of liquids therethrough, the backsheet 46 may optionally be omitted from the absorbent chassis 44.

The absorbent chassis 44 is generally conformable and capable of absorbing and retaining body exudates. The absorbent chassis 44 may have any of a number of shapes and sizes. For example, as representatively illustrated in FIG. 3, the absorbent chassis 44 may be rectangular, I-shaped or T-shaped. The size and absorbent capacity of the absorbent chassis 44 should be compatible with the size of the intended wearer and the fluid loading imparted by the intended use of the diaper 20. Typically, it is desirable that the absorbent chassis 44 have an absorbent capacity of at least about 300 grams of urine. It is generally preferred that the absorbent chassis 44 be narrower in the crotch region 26 than in the waist regions 22 and 24. It has been found that the absorbent chassis 44 of the present invention is particularly useful when the width dimension in the crotch region 26 is from about 2.5 to about 10.2 centimeters (1.0 to about 4.0 inches), desirably no more than about 7.6 centimeters (3.0 inches) and more desirably no more than about 5.1 centimeters (2.0 inches). The narrow crotch width dimension of the absorbent chassis 44 allows the absorbent chassis 44 to better fit between the legs of the wearer.

The bodyside liner 48 of the absorbent chassis 44, as representatively illustrated in FIG. 3, suitably presents a bodyfading surface which is intended to be worn adjacent the body of the wearer and is compliant, soft feeling and nonirritating to the wearer's skin. Further, the bodyside liner 48 may be less hydrophilic than the absorbent core 50, to present a relatively dry surface to the wearer, and may be sufficiently porous to be liquid permeable, permitting liquid to readily penetrate through its thickness. A suitable bodyside liner 48 may be manufactured from a wide selection of web materials, such as woven and nonwoven fabrics, porous foams, reticulated foams, apertured plastic films, natural fibers (for example, wood or cotton fibers), synthetic fibers (for example, polyester or polypropylene fibers), or a combination of natural and synthetic fibers. The bodyside liner 48 is suitably employed to help isolate the wearer's skin from fluids held in the absorbent core 50 of the absorbent chassis 44.

The backsheet 46 of the absorbent chassis 44, as representatively illustrated in FIG. 3, may suitably be composed of a material which is either liquid permeable or liquid impermeable. It is generally preferred that the backsheet 46 be formed from a material which is substantially impermeable to fluids. A typical backsheet can be manufactured from a thin plastic film or other flexible liquid-impermeable material. The backsheet 46 may also be constructed of a material which is similar to the material described as being suitable for the outer cover 42.

The bodyside liner 48 and backsheet 46 are generally adhered to one another so as to form a pocket in which the absorbent core 50 is located to provide the absorbent chassis 44. The bodyside liner 48 and backsheet 46 may be adhered directly to each other around the outer periphery of the absorbent chassis 44 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 48 to the backsheet 46. It should be noted that both the bodyside liner 48 and the backsheet 46 need not extend completely to the outer periphery of the absorbent chassis 44. For example, the backsheet 46 may extend to the outer periphery of the absorbent chassis 44 while the bodyside liner 48 may be attached to the backsheet 46 inboard of the outer periphery of the absorbent chassis 44, or more towards the longitudinal centerline of the diaper 20. In alternative configurations, especially wherein the backsheet 46 is omitted, the bodyside liner 48 may be suitably adhered directly to the absorbent core 50 or to the outer cover 42.

The absorbent core 50, as representatively illustrated in FIG. 3, is positioned between the bodyside liner 48 and the backsheet 46 to form the absorbent chassis 44. The absorbent core 50 is desirably conformable and capable of absorbing and retaining body exudates. The absorbent core 50 may have any of a number of shapes and sizes. For example, the absorbent core may be rectangular, I-shaped or T-shaped. It is generally preferred that the absorbent core 50 be narrower in the crotch region 26. The size of the absorbent core 50 should be compatible with the size of the intended wearer and the desired absorbent capacity of the absorbent chassis 44.

The absorbent core 50 of the absorbent chassis 44 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 50 may also comprise selected blends of the various types of fibers mentioned above.

In a particular aspect of the invention, the absorbent core 50 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 50 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 50 may comprise a laminate of fibrous webs and high-absorbency material or other suitable means of maintaining a high-absorbency material in a localized area.

As representatively illustrated in FIG. 3, the absorbent chassis 44 of the disposable diaper 20 may include a pair of containment flaps 54 which are configured to provide a barrier to the lateral flow of body exudates. The containment flaps 54 may be located along the laterally opposed side edges of the absorbent chassis 44. Each containment flap 54 typically defines an unattached edge which is configured to maintain an upright, perpendicular configuration in at least the crotch region 26 of the diaper 20 to form a seal against the wearer's body. The containment flaps 54 may extend longitudinally along the entire length of the absorbent chassis 44 or may only extend partially along the length of the absorbent chassis 44. When the containment flaps 54 are shorter in length than the absorbent chassis 44, the containment flaps 54 can be selectively positioned anywhere along the side edges of the absorbent chassis 44. In a particular aspect of the invention, the containment flaps 54 extend along the entire length of the absorbent chassis 44 to better contain the body exudates.

Such containment flaps 54 are generally well known to those skilled in the art. For example, suitable constructions and arrangements for containment flaps 54 are described in U.S. Pat. No. 4,704,116 issued Nov. 3, 1987, to K. Enloe the disclosure of which is hereby incorporated by reference.

The disposable diaper 20 of the different aspects of the present invention may further include elastics at the waist edges 32 and side edges 30 of the diaper 20 to further prevent the leakage of body exudates and support the absorbent chassis 44. For example, as representatively illustrated in FIG. 3, the diaper 20 of the present invention may include a pair of leg elastic members 52 which are connected to the laterally opposed side edges 30 in the crotch region 26 of the diaper 20 and a pair of waist elastic members 56 which are connected to the longitudinally opposed waist edges 32 of the diaper 20. The leg elastics 52 and waist elastics 56 are generally adapted to fit about the legs and waist of a wearer in use to maintain a positive, contacting relationship with the wearer to effectively reduce or eliminate the leakage of body exudates from the diaper 20.

Materials suitable for use as the leg elastics 52 and waist elastics 56 are well known to those skilled in the art. Exemplary of such materials are sheets or strands or ribbons of a apolymeric, elastomeric material which are adhered to the outer cover 42 in a stretched position, or which are attached to the outer cover 42 while the outer cover is pleated, such that elastic constrictive forces are imparted to the outer cover 42. The leg and waist elastics may also include such materials as polyurethane, synthetic and natural rubber or latent elastic materials described herein as being suitable for the adjustable belt.

The absorbent article of the different aspects of the present invention further includes a multi-functional fastening system 60 for securing the absorbent article about the waist of the wearer. The multi-functional fastening system includes fasteners located on one of the waist regions 22 and 24 of the diaper 20 which are configured to releasably engage the opposite waist region of the diaper 20 to maintain the diaper about the waist of the wearer. The use of fasteners which are refastenable or releasably engageable allows for ease of securing and removing the diaper 20 from the waist of the wearer.

As representatively illustrated in FIGS. 1–4, the multi-functional fastening system 60 of the present invention may include a pair of primary fasteners 62 which are located on the side edges 30 of the diaper 20 in the back waist region 24 of the diaper 20. In such a configuration, the primary fasteners 62 are configured to encircle the hips of the wearer and engage the outer surface 36 of the front waist region 22 of the diaper 20 to maintain the diaper 20 on the wearer. Alternatively, the primary fasteners 62 may be located on the front waist region 22 and may be configured to releasably engage the outer surface 36 of the back waist region 24 of the diaper 20.

Desirably, the primary fasteners 62 are releasably engageable directly with the outer surface of the outer cover 42 of the diaper 20 to provide improved ease of fastening. Alternatively, as representatively illustrated in FIGS. 1–4, the disposable diaper 20 of the present invention may further include an attachment panel 68 located on the outer cover 42 in one of the waist regions 22 and 24 of the diaper 20. In such a configuration, the primary fasteners 62 are releasably engageable with the attachment panel 68 to maintain the diaper 20 about the waist of the wearer. When the primary fasteners 62 are releasably engaged, the side edges 30 of the diaper 20 define leg openings which are configured to encircle the legs of the wearer and the waist edges 32 define a waist opening which is configured to encircle the waist of the wearer. As illustrated in FIG. 4, the attachment panel 68 may include two separate panels located along the opposite side edges in one of the waist regions 22 and 24 of the diaper 20. Alternatively, the attachment panel 68 may include a single piece of material which extends substantially across the respective waist edge 32 of the diaper 20.

In a particular embodiment, the primary fasteners 62 are configured to be releasably engaged with the outer surface of the opposite waist region 22 and 24 of the diaper 20 before the diaper 20 is placed on the wearer to provide a prefastened diaper. In such a configuration, the prefastened diaper 20 can be pulled on or off over the legs and hips of the wearer. If the diaper 20 becomes soiled during use, the primary fasteners 62 can be disengaged to easily remove the diaper 20 from the waist of the wearer with reduced risk of undesirably soiling the clothes or legs of the wearer. Thus, in such a configuration, the diaper 20 of the different aspects of the present invention can be configured to be pulled on or off over the hips of the wearer such as conventional training pants and can be applied to or removed by disengaging the fasteners similar to conventional diaper articles.

The multi-functional fastening system 60 on the disposable diaper 20 of the present invention includes an adjustable belt having a pair of secondary fasteners thereon to provide improved securement of the diaper 20 about the waist of the wearer after the primary fasteners 62 have been releasably engaged. The adjustable belt and secondary fasteners of the present invention are configured to further conform the waist regions 22 and 24 of the diaper 20 to the waist of the wearer. For example, as representatively illustrated in FIGS. 1–4, the diaper 20 may include an adjustable belt 64 which includes a pair of secondary fasteners 66 located on the opposed end portions of the adjustable belt 64.

The adjustable belt 64 and secondary fasteners 66 are located in one of the waist regions 22 and 24 of the diaper 20 and are configured to encircle the hips of the wearer and engage the outer surface 26 in the opposite waist region 22 and 24 of the diaper 20. For example, the adjustable belt 64 and secondary fasteners 66 may be located along the waist edge 32 of the diaper 20 in the back waist region 24 of the diaper 20. In such a configuration, the adjustable belt 64 and secondary fasteners 66 are configured to encircle the hips of the wearer and engage the outer surface 36 of the front waist region 22 of the diaper 20 to maintain the diaper 20 on the wearer. Alternatively, the adjustable belt 64 and secondary fasteners 66 may be located on the front waist region 22 A 15 and may be configured to releasably engage the outer surface 36 of the back waist region 24 of the diaper 20.

Desirably, the secondary fasteners 66 are releasably engageable directly with the outer surface of the outer cover 42 of the diaper 20 to provide improved ease of fastening. Alternatively, as described above and representatively illustrated in FIG. 4, the diaper 20 olf the present invention may further include an attachment panel 68 located on the outer cover 42 in one of the waist regions 22 and 24 of the diaper 20. In such a configuration, the secondary fasteners 66 may also be releasably engageable with the attachment panel 68 to maintain the diaper 20 about the waist of the wearer.

The use of such an adjustable belt 64 with secondary fasteners 66 has been found to be particularly desirable when the diaper 20 includes primary fasteners 62 which are releasably engaged with the respective waist region of the diaper 20 to provide a prefastened diaper which can be pulled on over the legs and hips of the wearer. In such a configuration, the waist opening of the diaper 20 when the primary fasteners 62 are engaged must be sufficient to allow the prefastened diaper to be pulled over the hips of the wearer. However, the circumference of the waist of the wearer is typically less than the circumference around the hips of the wearer. Thus, the waist opening of the prefastened diaper may not conform to the waist of the wearer which may undesirably result in leaks. In such a configuration, the adjustable belt 64 and secondary fasteners 66 of the diaper 20 of the present invention are configured to conform the waist regions of the diaper 20 to the wearer after the prefastened diaper is pulled on the wearer. Thus, the care giver is not required to reposition the primary fasteners 62 to conform the waist regions 22 and 24 to the waist of the wearer. As a result, when the diaper 20 is to be removed from the wearer, the care giver may simply disengage the secondary fasteners 66 if necessary and pull the prefastened diaper down over the hips and legs of the wearer without having to reposition the primary fastener 62, Alternatively, the care giver may disengage both the secondary and the primary fasteners 66 and 62 to remove the diaper in a manner similar to conventional diapers. In some configurations, the diaper may otherwise be pulled down without disengaging either of the fasteners 62 and 66 as the belt 64 may elongate a sufficient amount to allow the diaper 20 to be pulled down over the hips of the wearer.

In such configurations, the adjustable belt 64 and secondary fasteners 66 are intended to maintain the diaper 20 in a close conforming fit about the waist of the wearer to reduce the leakage of body exudates when in use. The primary fasteners 62 are intended to maintain the front and back waist regions 22 and 24 of the diaper 20 connected in such a manner that the diaper 20 can be pulled on or off over the hips of the wearer after the secondary fasteners 66 have been disengaged. The secondary fasteners 66 may also be selectively disengaged to facilitate inspection of the diaper 20 to determine if it has been soiled. The primary fasteners 62 can also provide a "child proofing function" by maintaining the diaper 20 at least partially secured about the waist of the wearer if the wearer disengages the secondary fasteners 66.

The secondary fasteners 66 may also provide improved fit when the diaper 20 is applied from an unfastened configuration similar to conventional diapers. For example, upon the initial fastening about the wearer, the primary fasteners 62 may be difficult to locate correctly due to the activity of the wearer. Thus, in such situations, the secondary fasteners can be used to provide a better conforming fit after the primary fasteners 62 have been engaged.

Suitable fasteners are well known to those skilled in the art and can include adhesive tape tab fasteners, hook and loop fasteners, mushroom fasteners, snaps, pins, belts and the like, and combinations thereof. For example, as representatively illustrated in FIGS. 1–4, the primary fasteners 62 and secondary fasteners 66 may be hook type fasteners and the outer cover 42 or attachment panel 68 may be configured to function as a complimentary loop type fastener. Desirably, the fasteners 62 and 66 are hook type fasteners which are releasably engageable directly with the outer cover 42. Such an arrangement provides the ability to vary the size of the waist opening in very small increments over a wide range to fit the waist of the wearer. In a particular embodiment, the primary and secondary fasteners 62 and 64 on each side of the diaper 20 may be provided by a single piece of material having a line of perforations separating the fasteners 62 and 64 for improved manufacturability. In an alternative arrangement wherein the diaper 20 is provided in a prefastened configuration, the primary fasteners 62 may comprise a releasable bond such as an ultrasonic point bond which can be selectively disengaged.

The fasteners may have any shape and size which provides the desired fastening of the diaper 20 about the waist of the wearer. It is further desirable that the outer surface of the secondary fasteners 66 provide a visual cue to the care giver as to their location. For example, in one embodiment, the secondary fasteners 66 are of a different color than the outer surface of the diaper 20 to enable the care giver to easily determine the location of the secondary fasteners 66. The primary fasteners 62 could also be of a different color than the secondary fasteners 66 and outer surface of the diaper 20.

Materials suitable for use as the adjustable belt 64 of the different aspects of the present invention are similar to those materials described above as being suitable for the outer cover 42. Desirably, the adjustable belt 64 is made of an elastic material which is capable of elongating at least about 25 percent and more desirably at least about 50 percent to provide improved fit about the waist of the wearer. For example, the adjustable belt 64 may comprise a neck bonded laminate material which includes a KRATON film material commercially available from the Dow Chemical Company, a business having offices located in Midland, Michigan. Alternatively, the adjustable belt 64 may include portions which include elastic material and portions which include inelastic material.

Desirably, the adjustable belt 64 is made of a latent elastic material which can be activated after the diaper 20 is manufactured. The use of such a latent elastic material eliminates the need to maintain the adjustable belt 64 in a tensioned condition as the diaper is manufactured. Suitable latent elastic materials are known to those skilled in the art. For example, suitable latent elastic materials are commercially available from Exxon under the trade designation EXX601. Alternative latent elastic materials are described in U.S. patent application Ser. No. 08/854,934 filed May 13, 1997 and entitled "IMPROVED COMPOSITE ELASTIC MATERIAL AND PROCESS FOR PRODUCING THE SAME", the disclosure of which is hereby incorporated by reference. The latent elastic material may be activated by a variety of methods known to those skilled in the art. For example, the latent elastic adjustable belts may be activated by heating the diaper after it is manufactured to cause the material to retract.

The primary fasteners 62, adjustable belt 64 and secondary fasteners 66 may be incorporated into the diaper 20 of the different aspects of the present invention in a variety of different manners known to those skilled in the art. For example, in the illustrated embodiments and as described above, the diaper 20 further includes a pair of belt loops 70 which define a pair of longitudinally opposed end portions 72. The end portions 72 of the belt loops 70 are attached directly or indirectly to the outer cover 42 such that the adjustable belt 64 is slidably contained between the belt loops 70 and the outer cover 42. For example, as representatively illustrated in FIGS. 1–4, the ends portions 72 of the belt lomp 70 may be aUaGhed to the bodyfacing surface of the outer cover 42 such that the adjustable belt 64 is located in the diaper 20 between the outer cover 42 and absorbent chassis 44 in one of the waist regions 22 and 24. Thus, in the illustrated embodiments, the majority of the adjustable belt 64 extends along the bodyfacing surface of the outer cover 42 between the outer cover 42 and the absorbent chassis 44 for improved aesthetics.

Alternatively, the adjustable belt 64 may extend along the garment facing surface of the outer cover 42, along the bodyside liner 48 between the absorbent chassis 44 and the wearer or between any of the layers of the absorbent chassis 44. For example, the belt loops may be attached to the absorbent chassis 44 or bodyside liner 48 and thus be indirectly attached to the bodyfacing surface of the outer cover 42. The longitudinal ends 72 of the belt loops 70 may suitably be attached to the diaper 20 using attachment methods described herein. For example, the ends 72 of the belt loops 70 may be ultrasonically bonded to the outer cover 42 or bodyside liner 48.

When the belt loops 70 are attached to the bodyfacing surface of the outer cover 42 as illustrated in FIGS. 1–4, the primary fasteners 62 are desirably located on the bodyfacing surface of the belt loops 70 or the belt loops 70 are made of fastener material for improved manufacturing efficiency and reduced cost. In such a configuration, the secondary fasteners 66 are desirably positioned laterally outward from and adjacent to the side edges of the outer cover 42, the belt loops 70 and the primary fasteners 62 for improved control and ease of fastening. Alternatively, the primary fasteners 62 may be attached to any of the other components of the diaper 20 such as the outer cover 42. The primary fasteners 62 may be adhered to the diaper 20 by any means known to those skilled in the art such as adhesive bonds, sonic bonds or thermal bonds. The secondary fasteners 66 may also be suitably connected to the end portions of the adjustable belt 64 using similar means.

The adjustable belt 64 may also be elongated before the belt loops 70 are attached to the outer cover 42 to provide a pretension to the adjustable belt 64 between the belt loops 70. For example, the adjustable belt 64 may be elongated from about 5 to about 100 percent before the belt loops 70 are attached to provide the desired pretension. However, as discussed above, it is desirable that the adjustable belt 64 be made from a latent elastic material which can be elastically activated after the diaper is manufactured for improved process control.

A portion of the adjustable belt 64 between the side edges of the outer cover 42 may be secured to the other portions of the diaper 20 such as the interior surface of the outer cover 42 to provide an attached portion 74 as illustrated in FIG. 4. The attached portion 74 of the adjustable belt 64 may be secured using methods known to those skilled in the art such as adhesive, sonic or thermal bonding. Desirably, the attached portion 74 defines an attaehed length 76 as illustrated in FIG. 4 which is less than about 75 percent and more desirably less than about 50 percent of the total length of the adjustable belt 64. Such an attached length provides sufficient securement of the adjustable belt to the diaper 20 without adversely affecting the ability of the adjustable belt to conform to the waist of the wearer to provide the improved fit.

The adjustable belt 64 may define any length and width which provide the desired improved fastening and fit about the wearer. For example, the adjustable belt 64 may define a length which is from about 7 to about 45 centimeters and a width which is from about 1 to about 10 centimeters. Desirably, the adjustable belt 64 defines a length which is slightly less than the width of the diaper 20 at the respective waist region after it has been activated if the belt is a latent elastic material such that the adjustable belt 64 is slightly elongated to pretension the waist region. The distance between the attached portions of the longitudinal ends 72 of the belt loops 70 is greater than the width of the adjustable belt 64 such that the adjustable belt is slidably contained between the belt loops 70. The secondary fasteners 66 on the ends of the adjustable belt 64 desirably define a width which is greater than the width of the adjustable belt 64 such that the secondary fasteners 66 can prevent the belt 64 from passing through the belt loops 70.

Materials suitable for use as the belt loops 70 of the different aspects of the present invention are similar to those materials described above as being suitable for the outer cover 42. As discussed above, the belt loops 70 desirably include a fastener material, such as a hook material, on one surface thereof to provide the primary fasteners 62. Suitable fastener materials for use as the belt loops 72 are set forth above as being suitable for the fasteners 62 and 66. The belt loops 70 may be a single material such as the hook material or may indude a composite of materials. For example, the belt loops 70 may comprise a composite material commercially which includes the combination of a nonwoven material and a fastener material. In such a configuration, the fastener material need not extend along the entire surface of the belt loop 70 to provide the primary fasteners 62. For example, the belt loops 70 may include fastener material such as hook material along the longitudinal ends 72 of the belt loops and not in the middle section of the belt loops 70.

If it is desired that the absorbent arcide of the present invention be prefastened, the absorbent article of the present invention may further include a pair of releasable side bonds (not shown) for improved reliability of maintaining the article in the prefastened condition particularly when it is being pulled on or off over the hips of the wearer. Absorbent articles including such releasable side bonds are further described in U.S. patent application entitled "DISPOSABLE ABSORBENT ARTICLES HAVING PASSIVE SIDE BONDS AND ADJUSTABLE FASTENING SYSTEMS" filed in the name of Elsberg on the same date as the instant application and having, the disclosure of which is hereby incorporated by reference. For example, the diaper 20 may include a pair of releasable side bonds which releasably connect the side edges 30 of the diaper in the front and back waist regions 22 and 24 of the diaper 20. The locaiorn of the releasable side bonds can be selectively varied to tailor the fit of the diaper for different sized wearers.

In such a configuration, the releasable side bonds can assist the fastening system 60 in maintaining the diaper 20 in a prefastened condition as the diaper 20 is pulled up or down over the hips of the wearer. Moreover, the releasable side bonds can prevent movement and shifting of the waist regions 22 and 24 relative to each other for improved fit and performance. The releasable side bonds can also prevent rollover or folding of the side edges 30 and waist edges S2 of the diaper 20 as it is pulled over the wearers hips.

The different aspects of the present invention advantageously provide disposable absorbent articles having a fastening system which includes an adjustable belt and methods of making the same. The fastening system may be prefastened to releasably engage the front and back waist portions to allow the absorbent article to be pulled up or down over the hips of the wearer such as conventional training pants. Moreover, the adjustable belt of the fastening system can be used to further conform the front and back waist portions of the absorbent article to maintain the absorbent article about the waist of the wearer after the article has been pulled on in a similar manner to conventional diapers.

As a result, the absorbent article of the present invention is designed to conform to the body of the wearer to effectively contain bodily exudates while still being capable of being reliably pulled up or down over the hips of the wearer to assist in the toilet training of the wearer. Moreover, similar to conventional diapers, the absorbent article of the present invention can advantageously be applied to and removed from the wearer with relative ease and cleanliness.

While the invention has been described in detail with respect to specific aspects thereof, iit will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A disposable absorbent article which defines an absorbent, a front waist region, a back waist region, and a crotch region which extends between and connects said waist regions, said absorbent article further comprising:

a) an adjustable belt located in one of said waist regions of said absorbent article wherein said adjustable belt is elastically elongatable and defines a pair of opposed end portions and a fastener on each of said opposed end portions; and b) a belt loop located inward from and adjacent to each of said fasteners on said adjustable belt to provide a pair of belt loops wherein each of said belt loops define a pair of opposed longitudinal ends which are attached to said one waist region of said absorbent article to slidably contain said adjustable belt between said belt loops and said one waist region and wherein said fasteners on said adjustable belt are configured to releasably engage an opposite one of said waist regions of said absorbent article.

2. The absorbent article of claim 1 wherein said fasteners are hook material of a hook and loop fastener.

3. The absorbent article of claim 1 wherein said absorbent article further includes an attachment panel located on a garment faceable surface of said article in said opposite waist region and wherein said fasteners on said adjustable belt are configured to releasably engage said attachment panel.

4. The absorbent article of claim 1 wherein said adjustable belt is capable of elongating at least about 50 percent.

5. The absorbent article of claim 1 wherein said longitudinal ends of said belt loops are attached to said one waist region using ultrasonic bonding.

6. The absorbent article of claim 1 wherein said fasteners on said opposed end portions of said adjustable belt define a width which is greater than a distance on said belt loops between said attached longitudinal ends.

7. The absorbent article of claim 1 wherein said adjustable belts includes a latent elastic material.

8. The absorbent article of claim 1 wherein each of said belt loops includes a fastener material which is configured to releasably engage said opposite waist region of said absorbent article.

9. The absorbent article of claim 8 wherein said adjustable belt is configured to be elongated and said pair of fasteners on said opposed end portions of said adjustable belt are configured to releasably engage said opposite waist region of said absorbent article after said fastener material on said belt loops has been releasably engaged to said opposite waist region to further conform said waist regions to a wearer's body after said absorbent article has been placed on said wearer.

10. The absorbent article of claim 1 wherein a portion of said adjustable belt between said belt loops is attached to said one waist region of said absorbent article.

11. The absorbent article of claim 10 wherein said attached portion of said adjustable belt defines an attached length which is less than about 75 percent of a total length of said adjustable belt and wherein said attached portion of said adjustable belt is located along a longitudinal centedine of said absorbent article.

12. A disposable absorbent article which defines an absorbent, a front waist region, a back waist region, a crotch region which extends between and connects said waist regions, a pair of opposed side edges and a pair of opposed waist edges, said absorbent article further comprising:
    a) an outer cover which defines a body faceable surface and a garment faceable surface;
    b) an adjustable belt located in one of said waist regions of said absorbent article wherein said adjustable belt defines a pair of opposed end portions;
    c) a fastener on each of said opposed end portions of said adjustable belt; and
    d) a belt loop located inward from and adjacent to each of said fasteners on said adjustable belt to provide a pair of belt loops wherein each of said belt loops defines a pair of longitudinally opposed ends which are attached to said body faceable surface of said outer cover in said one waist region of said absorbent article to slidably contain said adjustable belt between said belt loops and said body faceable surface of said outer cover and wherein said fasteners on said adjustable belt are configured to releasably engage said garment faceable surface of said outer cover in an opposite one of said waist regions of said absorbent article.

13. The absorbent article of claim 12 wherein said fasteners are hook material of a hook and loop fastener.

14. The absorbent article of claim 12 wherein said outer cover includes an attachment panel located on said garment faceable surface of said outer cover and wherein said fasteners on said adjustable belt are configured to releasably engage said attachment panel.

15. The absorbent article of claim 12 wherein said adjustable belt is capable of elongating at least about 50 percent.

16. The absorbent article of claim 12 wherein said longitudinal ends of each of said belt loops are attached to said outer cover using ultrasonic bonding.

17. The absorbent article of claim 12 wherein said fasteners define a width which is greater than a distance on said belt loops between said attached longitudinal ends.

18. The absorbent article of claim 12 wherein said fasteners define a width which is greater than a width of said adjustable belt.

19. The absorbent article of claim 12 wherein said adjustable belt includes a latent elastic material.

20. The absorbent article of claim 12 wherein said adjustable belt is configured to provide a pretension on said absorbent article between said belt loops.

21. The absorbent article of claim 12 wherein each of said belt loops includes a primary fastener on a body faceable surface of said belt loops which is configured to releasably engage said garment faceable surface of said outer cover in said opposite waist region.

22. The absorbent article of claim 21 wherein said adjustable belt is configured to be elongated and said fasteners on said adjustable belt are configured to releasably engage said garment faceable surface of said outer cover in said opposite waist region of said absorbent article after said primary fasteners have been releasably engaged to further conform said waist regions to a wearer's body after said absorbent article has been placed on said wearer.

23. The absorbent article of claim 21 wherein said primary fasteners are hook material of a hook and loop fastener.

24. The absorbent article of claim 21 wherein said outer cover includes an attachment panel located on said garment faceable surface of said outer cover and wherein said primary fasteners on said belt loops are configured to releasably engage said attachment panel.

25. A prefastened disposable absorbent article which defines an absorbent, a front waist region, a back waist region, a crotch region which extends between and connects said waist regions, a pair of opposed side edges and a pair of opposed waist edges, said absorbent article further comprising:
    a) an outer cover which defines a body faceable surface and a garment faceable surface;
    b) an adjustable belt located in one of said waist regions of said absorbent article wherein said adjustable belt defines a pair of opposed end portions;
    c) a secondary fastener on each of said opposed end portions of said adjustable belt;
    d) a belt loop located inward from and adjacent to each of said secondary fasteners on said adjustable belt to provide a pair of belt loops wherein each of said belt loops defines a pair of longitudinally opposed ends which are attached to said outer cover in said one waist region of said absorbent article to slidably contain said adjustable belt between said belt loops and said outer cover; and
    e) a primary fastener on each of said belt loops which is releasably engaged to said outer cover in said waist region opposite said one waist region to provide said prefastened absorbent article wherein said secondary fasteners on said adjustable belt are configured to releasably engage said outer cover in said opposite one of said waist regions of said absorbent article to further conform said waist regions to a wearer's body after said prefastened absorbent article has been placed on said wearer.

26. The prefastened absorbent article of claim 25 wherein said longitudinal ends of each of said belt loops are attached to a body faceable surface of said outer cover in said one waist region to slidably contain said adjustable belt between said belt loops and said body faceable surface of said outer cover.

27. The prefastened absorbent article of claim 26 wherein said primary fasteners are attached to a body faceable surface of said belt loops and are releasably engaged to said garment facing surface of said outer cover.

28. The prefastened absorbent article of claim 25 wherein said primary fasteners and said secondary fasteners are hook material of a hook and loop fastener.

29. The prefastened absorbent article of claim 25 wherein said outer cover includes an attachment panel located on said garment faceable surface of said outer cover and wherein said primary fasteners are releasably engaged to said attachment panel.

30. The prefastened absorbent article of claim 25 wherein said secondary fasteners define a width which is greater than a distance on said belt loops between said attached longitudinal ends.

31. The absorbent article of claim 30 wherein said adjustable belt is configured to provide a pretension on said absorbent article between said belt loops.

32. The prefastened absorbent article of claim 25 wherein said adjustable belt includes a latent elastic material.

* * * * *